(12) United States Patent
Pfau et al.

(10) Patent No.: US 12,248,861 B2
(45) Date of Patent: Mar. 11, 2025

(54) ANTISYMMETRIC NEURAL NETWORKS

(71) Applicant: DeepMind Technologies Limited, London (GB)

(72) Inventors: David Benjamin Pfau, London (GB); James Spencer, London (GB); Alexander Graeme de Garis Matthews, London (GB)

(73) Assignee: DeepMind Technologies Limited, London (GB)

( * ) Notice: Subject to any disclaimer, the term of this patent is extended or adjusted under 35 U.S.C. 154(b) by 817 days.

(21) Appl. No.: 17/011,569

(22) Filed: Sep. 3, 2020

(65) Prior Publication Data

US 2021/0064961 A1  Mar. 4, 2021

Related U.S. Application Data

(60) Provisional application No. 62/895,491, filed on Sep. 3, 2019.

(51) Int. Cl.
*G06N 3/04* (2023.01)
*G06F 17/18* (2006.01)

(52) U.S. Cl.
CPC ............... *G06N 3/04* (2013.01); *G06F 17/18* (2013.01)

(58) Field of Classification Search
CPC .......... G06N 3/04; G06N 3/045; G06N 3/084; G06F 17/18; G16C 20/70; G16C 10/00
See application file for complete search history.

(56) References Cited

U.S. PATENT DOCUMENTS

| | | | | |
|---|---|---|---|---|
| 7,788,196 B2* | 8/2010 | Buscema | ............... | G06N 3/048 706/31 |
| 2021/0398621 A1* | 12/2021 | Stojevic | ................. | G16C 20/30 |
| 2022/0383992 A1* | 12/2022 | Triendl | ................... | G06N 3/045 |

OTHER PUBLICATIONS

Han, Jiequn, Linfeng Zhang, and E. Weinan. "Solving many-electron Schrödinger equation using deep neural networks." (2018) (Year: 2018).*
Bond, Benjamin Daniel. "A Comparative Analysis of Partial Least Squares (PLS) Regression and Artificial Neural Network (ANN) Methods for Determining Elemental Weights in Sheet Metal" (2014). (Year: 2014).*
Chang, Bo, et al. "Reversible architectures for arbitrarily deep residual neural networks." Proceedings of the AAAI conference on artificial intelligence. vol. 32. No. 1. 2018. (Year: 2018).*
Unke, Oliver T., and Markus Meuwly. "PhysNet: A neural network for predicting energies, forces, dipole moments, and partial charges." Journal of chemical theory and computation 15.6 (2019): 3678-3693. (Year: 2019).*
Zhai, Huanchen. Potential Energy Surface Exploration of Metal Catalytic Clusters. University of California, Los Angeles, 2019. (Year: 2019).*
Han, Jiequn, et al. "Universal approximation of symmetric and anti-symmetric functions." arXiv preprint arXiv:1912.01765 (2019). (Year: 2019).*

(Continued)

*Primary Examiner* — Vincent Gonzales
*Assistant Examiner* — Sidney Vincent Bostwick
(74) *Attorney, Agent, or Firm* — Fish & Richardson P.C.

(57) ABSTRACT

Methods, systems, and apparatus, including computer programs encoded on computer storage media, for processing inputs using antisymmetric neural networks.

23 Claims, 4 Drawing Sheets

(56) References Cited

OTHER PUBLICATIONS

Lo, Shih Chung B., et al. "Transformationally identical and invariant convolutional neural networks through symmetric element operators." arXiv preprint arXiv:1806.03636 (2018). (Year: 2018).*
Ognjanovski G. (2019). Everything you need to know about neural networks and backpropagation—Machine learning easy and fun. https://towardsdatascience.com/everything-you-need-to-know-about-neural-networks-and-backpropagation-machine-learning-made-easy-e5285bc2be3a (Year: 2019).*
International Preliminary Report on Patentability in International Appln. No. PCT/EP2020/074578, dated Mar. 8, 2022, 9 pages.
Amari, "Natural gradient works efficiently in learning," Neural Comput., Feb. 1998, 10(2):251-76.
Assaraf et al., "Optimizing the energy with quantum Monte Carlo: A lower numerical scaling for Jastrow-Slater expansions," Journal of chemical theory and computation, Nov. 2017, 14;13(11):5273-81.
Badinski et al., "Methods for calculating forces within quantum Monte Carlo simulations," Journal of Physics: Condensed Matter, Feb. 2010, 22(7):074202.
Bajdich et al., "We will list here the peer-reviewed publications that have used QWalk in one form or another," Phys. Rev. Lett., 2006, 96:130201.
Bartlett et al., "Coupled-cluster theory in quantum chemistry," Rev. Modern Phys., Feb. 2007, 79(1):291-352.
Booth et al., "Approaching chemical accuracy using full configuration interaction quantum Monte Carlo: a study of ionization potentials," J. Chem. Phys., May 2010, 132(17):174104.
Burton et al., "Holomorphic Hartree-Fock Theory: An Inherently Multireference Approach," J. Chem. Theory Comput., Jan. 2016, 12(1):167-73.
Carleo et al., "Solving the quantummany-body problemwith artificial neural networks," Science, Feb. 2017, 355(6325):602-6.
Cencek et al., "Benchmark calculations for He2+ and LiH molecules using explicitly correlated gaussian functions," Chem. Phys. Lett., Apr. 2000, 320(5-6):549-552.
Chakravorty et al., "Ground-state correlation energies for atomic ions with 3 to 18 electrons," Phys. Rev. A, May 1993, 47(5):3649.
Cheng et al., "A universal density matrix functional from molecular orbital-based machine learning: Transferability across organic molecules," J. Chem. Phys., 2019, 150:131103.
Choo et al., "Fermionic neural-network states for ab-initio electronic structure," Nature communications, May 2020, 11(1):1-7.
Choo et al., "Symmetries and many-body excita262 tions with neural-network quantum states," Phys. Rev. Lett., Oct. 2018, 121(16):167204.
Clark et al., "Computing the energy of a water molecule using multideterminants: A simple, efficient algorithm," The Journal of chemical physics, Dec. 2011, 135(24):244105.
Curtiss et al., "Gaussian-3 (G3) theory for molecules containing first and second-row atoms," J. Chem. Phys., Nov. 1998, 109(18):7764-7776.
Dash et al., "Perturbatively selected configuration-interaction wave functions for efficient geometry optimization in quan tum Monte Carlo," Journal of chemical theory and computation, Jun. 2018, 14(8):4176-82.
DePrince et al., "Accuracy and efficiency of coupled-cluster theory using density fitting / Cholesky decomposition, frozen natural orbitals, and a T1-transformed Hamiltonian," J. Chem. Theory Comput., Jun. 2013, 9(6):2687-96.
Feller et al., "Application of systematic sequences of wave functions to the water dimer," J. Chem. Phys., Apr. 1992, 96(8):6104-14.
Feynman et al., "Energy spectrum of the excitations in liquid helium," Physical Review, Jun. 1956, 102(5):1189.
Filippi et al., "Multiconfiguration wave functions for quantum Monte Carlo calculations of first-row diatomic molecules," J. Chem. Phys., Jul. 1996, 105(1):213-226.
Flyvbjerg et al., "Error estimates on averages of correlated data," J. Chem. Phys., Jul. 1989, 91(1):461-466.
Foulkes et al., "Quantum Monte Carlo simulations of solids," Rev. Modern Phys., Jan. 2001, 73(1):33.
Gdanitz et al., "Erratum to Accurately solving the electronic Schrodinger equation of atoms and molecules using explicitly correlated (r 1 2-) MR-CI: the ground state potential energy curve of N 2," Chemical Physics Letters, Feb. 1998, 288(2-4):590-2.
Gdanitz, "Accurately solving the electronic Schrodinger equation of atoms and molecules using explicitly correlated (r12-)MR-CI: the ground state potential energy curve of N2," Chem. Phys. Lett., Feb. 1998, 283(5-6):253-261.
Giles et al., "Collected matrix derivative results for forward and reverse mode algorithmic differentiation," In Advances in Automatic Differentiation, 2008, 35-44.
Gilmer et al., "Neural Message Passing for Quantum Chemistry," Proceedings of the 34th International Conference on Machine Learning, 2017, 0:1263-1272.
Giner et al., "Quantum Monte Carlo with reoptimised perturbatively selected configuration-interaction wave functions," Molecular Physics, Apr. 2016, 114(7-8):910-20.
Han et al., "Solving many-electron Schrodinger equation using deep neural networks," arXiv preprint arXiv:1807.07014, Dec. 2019, 399:108929.
Helgaker et al., "Basis-set convergence of correlated calculations on water," J. Chem. Phys., Jun. 1997, 106(23):9639-46.
Hermann et al., "Deep-neural-network solution of the electronic Schrödinger equation," Nature Chemistry, Oct. 2020, 12(10):891-7.
Hood et al., "Quantum monte carlo investigation of exchange and correlation in silicon," Physical review letters, Apr. 1997, 78(17):3350.
Kessler et al., "Artificial neural networks as trial wave 268 functions for quantum Monte Carlo," arXiv preprint arXiv:1904.10251, Apr. 2019, 14 pages.
Klopper et al., "Sub-meV accuracy in first286 principles computations of the ionization potentials and electron affinities of the atoms H to Ne," Physical Review A., Feb. 2010, 81(2):022503.
Krizhevsky et al., "Imagenet classification with deep convolutional neural networks," NeurIPS, May 2012, 60(6):84-90.
Le Roy et al., "An accurate analytic potential function for ground-state N2 from a direct-potential-fit analysis of spectroscopic data," J. Chem. Phys., Oct. 2006, 125(16):164310.
Lee et al., "Strategies for improving the efficiency of quantum Monte Carlo calculations," Physical Review E., Jun. 2011, 83(6):066706.
Lou et al., "Backflow Transformations via Neural Networks for Quantum Many-Body Wave-Functions," CoRR, Jul. 2018, arxiv.org/abs/1807.10770, 10 pages.
Luo et al., "Machine learning many-electron wave functions via backflow transformations," Phys. Rev. Lett., 2019, 122:226401.
Lyakh et al., "Multireference nature of chemistry: the coupled-cluster view," Chem. Rev., Jan. 2012, 112(1):182-243.
Martens et al., "Optimizing neural networks with Kronecker-factored ap274 proximate curvature," InInternational conference on machine learning, Jun. 2015, 2408-2417.
Mazzola et al., "Finite-temperature electronic simulations without the Born-Oppenheimer constraint," The Journal of chemical physics, Oct. 2012, 137(13):134112.
Mills et al., "Deep learning and the Schrödinger equation," Physical Review A., Oct. 2017, 96(4):042113.
Motta et al., "Ground-state properties of the hydrogen chain: insulator-to-metal transition, dimerization, and magnetic phases," arXiv preprint arXiv:1911.01618, Nov. 2019.
Motta et al., "Towards the solution of the many-electron problem in real materials: equation of state of the hydrogen chain with state-of-the-artmany-bodymethods," Phys. Rev. X, Sep. 2017, 7(3):031059.
Nagy et al., "Variational quantum Monte Carlo method with a neural264 network Ansatz for open quantum systems," Phys. Rev. Lett., Jun. 2019, 122(25):250501.
Needs et al., "Casino: User's Guide Version 2.13," Sep. 2019, pp. 180-181.
Neuscamman et al., "Optimizing large parameter sets in variational quantum Monte Carlo," Physical Review B., Jan. 2012, 85(4):045103.
Nomura et al., "Restricted Boltzmann machine learning for solving strongly correlated quantum systems," Physical Review B., Nov. 2017, 96(20):205152.

(56) References Cited

OTHER PUBLICATIONS

Orús et al., "A practical introduction to tensor networks: Matrix product states and projected entangled pair states," Annals of Physics, Oct. 2014, 349:117-58.

Otis et al., "Complementary first and second derivative methods 278 for Ansatz optimization in variational Monte Carlo," Phys. Chem. Chem. Phys., 2019, 21(27):14491-510.

Parrish et al., "Psi4 1.1: an open-source electronic structure program emphasizing automation, advanced libraries, and interoperability," J. Chem. Theory Comput., Jul. 2017, 13(7):3185-3197.

PCT International Search Report and Written Opinion in International Appln. No. PCT/EP2020/074578, dated Dec. 14, 2020, 15 pages.

Petz et al., "Geometries of quantum states," J. Math. Phys., Jun. 1996, 37(6):2662-2673.

Pfau et al., "Ab initio solution of the many-electron Schrödinger equation with deep neural networks," Physical Review Research, Sep. 2020, 2(3):033429.

Ramachandran et al., "Stand-Alone Self-Attention in Vision Models," 33rd Conference on Neural Information Processing Systems, 2019, 15 pages.

Ruggeri et al., "Nonlinear network description for many-body quantum systems in continuous space," Physical review letters, May 2018, 120(20):205302.

Sabzevari et al., "An accelerated linear method for optimizing non-linear wavefunctions in variational Monte Carlo," The Journal of Chemical Physics, Jan. 2020, 152(2):024111.

Saito et al., "Method to solve quantum few-body problems with artificial neural networks," J. Phys. Soc. Japan, Jul. 2018, 87(7):074002.

Schütt et al., " Quantum-chemical insights from deep tensor neural networks," Nature communications, Jan. 2017, 8(1):1-8.

Schütt et al., "SchNet—A deep learning architecture for molecules and materials," The Journal of Chemical Physics, Jun. 2018, 28;148(24):241722.

Schütt et al., "Unifying machine learning and quantum chemistry with a deep neural network for molecular wavefunctions," Nature Communications, Nov. 2019, 10(1):1-0.

Senior et al., "Improved protein structure prediction using potentials from deep learning," Nature, Jan. 2020, 577(7792):706-10.

Seth et al., "QuantumMonte Carlo study of the first-row atoms and ions," J. Chem. Phys., Feb. 2011, 134(8):084105.

Shawe-Taylor et al., "Building symmetries into feedforward networks," In1989 First IEE International Conference on Artificial Neural Networks, Oct. 1989, 158-162.

Silver et al., "Mastering the game of Go with deep neural networks and tree search," Nature, Jan. 2016, 529(7587):484-9.

Sinitskiy et al., "Physical machine learning outperforms human learning in Quantum Chemistry," arXiv preprint arXiv, Aug. 2019, 1908.00971.

Sorella et al., "Green function Monte Carlo with stochastic reconfiguration," Phys. Rev. Lett., May 1998, 80(20):4558.

Sun et al., "PySCF: the Python-based simulations of chemistry framework," Wiley Interdisciplinary Reviews: Computational Molecular Science, Jan. 2018, 8(1):e1340.

Taddei et al., "Iterative backflow renormalization procedure for many-body ground-state wave functions of strongly interacting normal Fermi liquids," Physical Review B, Mar. 2015, 91(11):115106.

Toulouse et al., "Optimization of quantum Monte Carlo wave functions by energy minimization," J. Chem. Phys., Feb. 2007, 126(8):084102.

Troyer et al., "Computational complexity and fundamental limitations to 245 fermionic quantum Monte Carlo simulations," Physical review letters, May 2005, 94(17):170201.

Umrigar et al., "A diffusion Monte Carlo algorithm with very small time-step errors," J. Chem. Phys., Aug. 1993, 99(4):2865-2890.

Van Voorhis et al., "Benchmark variational coupled cluster doubles results," J. Chem. Phys., Nov. 2000, 113(20):8873-8879.

Yang et al., "Deep learning-enhanced variational Monte Carlo method for quantum many-body physics," Physical Review Research, Feb. 2020, 2(1):012039.

Zhang et al., "Ab initio electronic structure calculations by auxiliary-field quantum Monte Carlo," Handbook of Materials Modeling: Methods: Theory and Modeling, 2020, 123-49.

Decision to Grant Patent in Japanese Appln. No. 2022-511314, dated Jul. 3, 2023, 5 pages.

\* cited by examiner

ANTISYMMETRIC NEURAL NETWORKS

CROSS-REFERENCE TO RELATED APPLICATION

This application claims priority to U.S. Provisional Application No. 62/895,491, filed on Sep. 3, 2019. The disclosure of the prior application is considered part of and is incorporated by reference in the disclosure of this application.

BACKGROUND

This specification relates to neural networks.

Neural networks are machine learning models that employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

SUMMARY

This specification describes a system implemented as computer programs on one or more computers in one or more locations that processes inputs using an antisymmetric neural network. Generally, the antisymmetric neural network is a neural network that is antisymmetric with respect to the inputs to the neural network. That is, if the relative positions of any two vectors in the network input are swapped, the output of the neural network after the swap will be equal in magnitude but opposite in sign to the output of the neural network before the swap.

In one aspect there is described a computer-implemented method comprising obtaining input data characterizing a system with a plurality of electrons, the input data comprising electron features for each of the plurality of electrons and pair features for each of a plurality of pairs of the plurality of electrons; and processing the input data using an antisymmetric neural network having a plurality of intermediate layers. The antisymmetric neural network may be configured to process the input data to generate as output a predicted value of one or more properties of the system; and each of the plurality of intermediate layers of the antisymmetric neural network may be configured to generate a respective layer output for the intermediate layer from a respective layer input to the intermediate layer by applying a respective permutation-equivariant function to the respective layer input.

One application of the described system and method is to predict the value of a wavefunction of a chemical system such as a molecule. Some known approaches to this problem work are accurate but do not scale well and are computationally impractical to apply to other than very small molecules. They can also be inaccurate on non-equilibrium geometries, which are important in practice. Variational Monte Carlo methods are less computationally intensive but suffer from low accuracy. Some neural network based approaches are trained with supervised learning, learning from examples generated by existing computational methods.

By contrast implementations of the described system and method can produce accurate results by including pairwise (exchange) interactions between each of the pairs of electrons as well as using features from each (single) electron. In principle such an approach is also computationally hard. However the described system and method has further recognized that the computational load can be mitigated by using an antisymmetric neural network, which is achieved by using intermediate layers which implement permutation-equivariant functions. This provides an Ansatz which is expressive but computationally feasible.

In some implementations for an intermediate layer (more particularly each of the plurality of intermediate layers except for a final intermediate layer), the respective layer input comprises a separate input stream for each of the electrons and for each of the pairs of electrons, the layer output comprises a separate output stream for each of the electrons and for each of the pairs of electrons, and the intermediate layer is configured to operate on each input stream with a corresponding stream sub-layer. For a first intermediate layer of the plurality of intermediate layers, the input stream for each of the electrons may be the electron features for the electron and the input stream for each of the pairs of electrons may be the pair features for the pair of electrons. This approach, with streams for electrons and for pairs of electrons, can facilitate controlling the computational requirements of the system.

In some implementations, for each of the plurality of intermediate layers, the particular stream sub-layer corresponding to each of the electrons is configured to: receive the input stream for the corresponding electron from the respective layer input, generate a combined input for the corresponding electron from the input streams from the respective layer input, concatenate the input stream generated by the particular stream sub-layer with the combined input to generate a concatenated input stream for the corresponding electron, and process the concatenated input stream to generate a concatenated output stream for the corresponding electron. (Put differently, depending on what are viewed as the input and output, the particular stream sub-layer may receive the input stream for the corresponding electron from the respective layer input; may process the input stream to generate an initial output stream; may generate a combined output for the corresponding electron from the initial output streams generated by the stream sub-layers of the particular intermediate layer; and may concatenate the initial output stream generated by the particular stream sub-layer with the combined output to generate a concatenated output stream for the corresponding electron). The concatenated output stream may comprise the output stream for the corresponding electron and/or, for at least one of the intermediate layers, the output stream for the corresponding electron may include the concatenated output stream and a residual output stream generated by the stream sub-layer for the corresponding electron in a preceding intermediate layer.

In some implementations processing the (concatenated) input stream to generate a concatenated output stream comprises applying a linear transformation to the (concatenated) input stream to generate a transformed stream, and applying a non-linear activation function to the transformed stream to generate the (concatenated) output stream. Generating a combined signal (input) for the corresponding electron may comprise, for each of a plurality of electron spins, e.g., spin-up and spin-down states, computing an average of the (input) streams corresponding to electrons that have the electron spin, and including the averages in the combined input. This may also comprise, for each of the plurality of electron spins, computing an average of the (input) streams corresponding to pairs of electrons that include the corresponding electron and an electron that has the electron spin, and including the averages in the combined input.

The antisymmetric neural network may be configured to generate the predicted value from the layer output of the last intermediate layer of the plurality of layers. Generating the predicted value may comprise generating, from the layer output of the last intermediate layer, a respective (matrix) input for each of a plurality of determinants, determining a respective output of each determinant from the respective input for the determinant, and determining the predicted value from the respective outputs of each of the determinants. Such a matrix input may comprise a square matrix of (all) permutations of the output streams for each of the electrons. In implementations generating the respective input (to the determinants) may also include applying a linear transformation (in particular, different for spin-up and spin-down states) to the layer output of the last intermediate layer to generate a final transformed output, and applying each of a plurality of exponentially-decaying envelopes to some or all of the final transformed output. This can help to enforce a boundary condition that the wavefunction goes to zero far away from the nuclei.

In implementations the system provides a mapping from electron features, e.g., positions of a set of spin-up and of a set of spin-down electrons, to values of the wavefunction, $\psi$, of the chemical system e.g., molecule. Thus the wavefunction may be mapped or characterized e.g., to determine an associated energy such as a ground state energy of the chemical system e.g., molecule. The associated electron probability density is given by $\psi^2$.

The system can be trained to optimize a variational energy e.g., to minimize the energy to determine a ground state wavefunction. This may be performed by optimizing parameters of the antisymmetric neural network using stochastic gradient descent on an objective function which estimates the energy from the wavefunction.

The wavefunction of the chemical system e.g., molecule can be used in many ways.

For example the wavefunction may be used to design a molecule or other chemical system (in silico), e.g., by screening a plurality of compound structures based on an energy of the ground state wavefunctions of the structures to assess which structures are likely to be relatively more stable than others. Optionally a molecule or other chemical system may then be synthesized according to the structure(s) identified as relatively more stable.

In another example the wavefunction may be used to select a synthetic route for a molecule or other chemical system. For example there may be more than one possible synthetic route, and a ground state energy of one or more intermediates of each synthetic route may be determined and compared to assess which synthetic route is likely to be easier. Or there may be more than one possible synthetic route, and an energy of one or more different conformations of the same intermediate in each synthetic route may be determined and compared to assess which synthetic route is likely to be easier (the techniques described herein can be useful in determining accurate wavefunctions for bent or twisted molecules). Optionally the molecule or other chemical system may then be synthesized using the easier synthetic route.

In another example a synthetic route for a molecule or other chemical system may be known but the reaction mechanism may be unknown. One or more wavefunctions and/or ground state energies may be determined for one or more components of one or more steps in a postulated mechanism, to evaluate a likelihood of the mechanism, and a mechanism for the reaction may be identified by comparing these. Once the reaction mechanism is known the reaction may be improved be adapting the mechanism; optionally a molecule or other chemical system may then be synthesized using the adapted mechanism.

In another example a conformation of a molecule or other chemical system may be identified by comparing wavefunctions and/or their energies for different postulated conformations. The molecule or other chemical system may then be modified to change the conformation or to make a desired conformation more likely; optionally the molecule or other chemical system may then be synthesized with the desired conformation.

In another example the wavefunction and/or ground state energy may be determined for one or both of a ligand and its target. The target may be a biomolecular target and the ligand may be a candidate drug, or the ligand may be a catalyst. The wavefunctions and/or ground state energies may be used to predict which ligands will interact strongly with the target; one or more of the ligands may then be synthesized for real-world evaluation.

In another example the wavefunction and energy may be determined for two or more different physical or electronic conformations of a molecule or other chemical system and a difference between the energies used to characterize the molecule/chemical system e.g., to identify an unknown molecule/chemical system or to design (and optionally then make) a molecule/chemical system with particular electromagnetic absorption or emission characteristics.

Particular embodiments of the subject matter described in this specification can be implemented so as to realize one or more of the following advantages.

Exact wavefunctions of interesting chemical systems are infeasible to compute because they are NP-hard to compute, but approximations can be found, e.g., using polynomially-scaling algorithms. A challenge for many of these algorithms is the choice of wavefunction approximation, or Ansatz, which must trade off between efficiency and accuracy.

While neural networks have generally shown impressive power as accurate function approximators, problems in electronic structure require wavefunctions that obey Fermi-Dirac statistics. This makes existing neural network architectures not suitable for approximating the wavefunction (or other properties that relate to the electronic structure) of a chemical system.

This specification introduces an antisymmetric neural network that can approximate a wavefunction (or other property) of a multi-electron system in a manner that obeys Fermi-Dirac statistics. By making use of the antisymmetric neural network, the described techniques are able to achieve accuracy beyond other variational quantum Monte Carlo wavefunction approximators on a variety of atoms and small molecules while using no data other than atomic positions and charges. The described techniques outperform other ab-initio quantum chemistry methods, allowing for accurate direct optimization of wavefunctions for previously intractable molecules and solids.

Antisymmetric neural networks can be constructed and optimized to enable high accuracy quantum chemistry calculations of challenging systems. For example, the antisymmetric neural network makes the simple and straightforward VMC method competitive with DMC, AFQMC and CCSD (T) methods for equilibrium geometries and better than CCSD(T) for many out-of-equilibrium geometries.

Advantageously, one network architecture with one set of training parameters has been able to attain high accuracy on many different chemical systems. Thus, the use of the antisymmetric neural network means that choosing a basis set or performing basis-set extrapolation for a new chemical system are not required, removing a common source of error in computational quantum chemistry.

More generally, making use of the antisymmetric neural network, i.e., a neural network that is antisymmetric with respect to the inputs to the neural network, can result in improved accuracy on many different tasks when the predictions of the neural network are required to have this antisymmetric property.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a system implemented as computer programs on one or more computers in one or more locations that processes inputs using an antisymmetric neural network. Generally, the antisymmetric neural network is a neural network that is antisymmetric with respect to the inputs to the neural network. That is, if the relative positions of any two vectors in the network input are swapped, the output of the neural network after the swap will be equal in magnitude but opposite in sign to the output of the neural network before the swap.

The neural network can be can be configured to receive any of a variety of digital data inputs and to generate any of a variety of scores for the digital data inputs.

In particular, in the description that follows, the neural network is described as being configured to receive as input data characterizing a chemical system, e.g., an atom, a molecule, or other group of one or more nuclei and multiple electrons, and as being configured to generate as output a prediction of one or more properties of the chemical system.

However, the neural network can also be configured to process other kinds of data from other systems including different components where the antisymmetric property described above is beneficial. For example, the input to the neural network may be data characterizing participants in a zero-sum game and the output of the neural network may be data representing predicted value functions for the zero-sum game.

As a particular example, although the description that follows describes that the outputs of the layers in the antisymmetric neural network are based on the spins of the electrons in the system, in a different context the outputs could be based on a different property of the components of the system.

Figure 1:
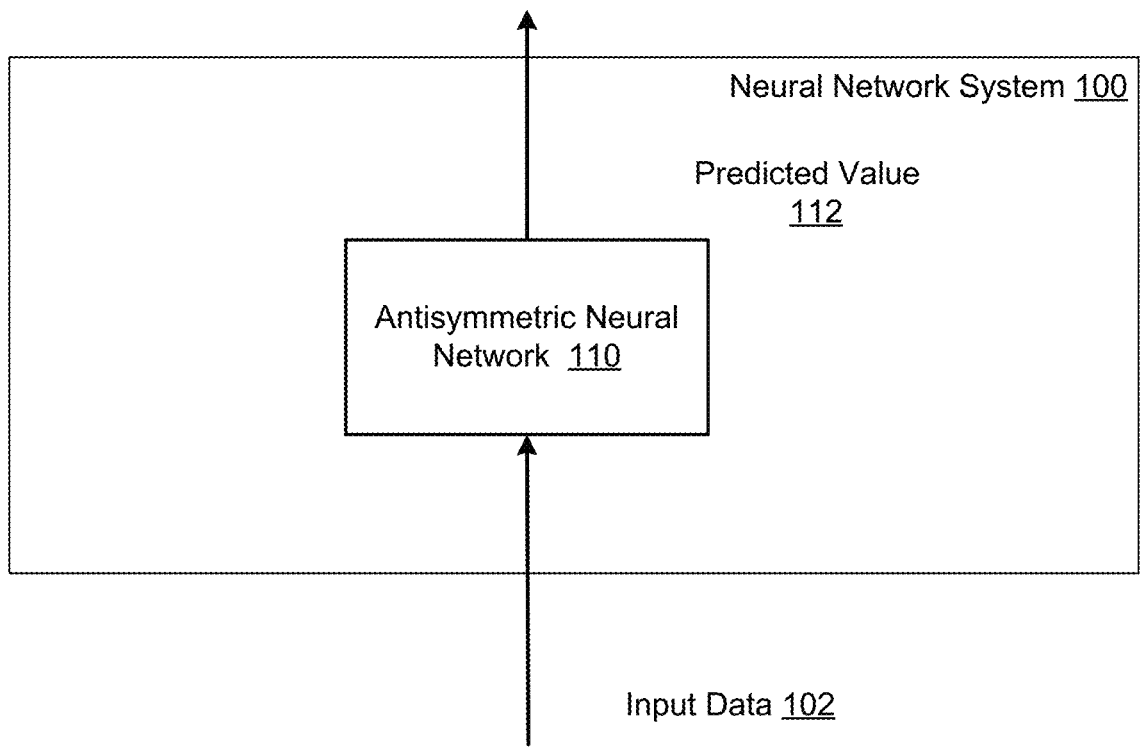
FIG. 1 shows an example neural network system.

FIG. 1 shows an example neural network system 100. The neural network system 100 is an example of a system implemented as computer programs on one or more computers in one or more locations, in which the systems, components, and techniques described below can be implemented.

The neural network system 100 is a system that obtains input data 102 characterizing a system with a plurality of components, e.g., a chemical system with a plurality of electrons.

The neural network system 100 then processes the input data 102 using an antisymmetric neural network 110 that is configured to process the input data 102 to generate as output a predicted value 112 of one or more properties of the system. When the system is a chemical system, the one or more properties can include the wavefunction of the chemical system. That is, the antisymmetric neural network 110 is configured to process the input data 102 characterizing the chemical system to generate an output 112 that is an estimate of the wavefunction of the chemical system.

Because the wavefunction of any chemical system must obey Fermi-Dirac statistics, i.e., the wavefunction must be antisymmetric under the simultaneous exchange of the position and spin coordinate of any two electrons in the chemical system, the neural network 110 must also be antisymmetric in order to accurately estimate the wavefunction.

As another example, the predicted value can be or can include the ground state energy of the chemical system.

The input data 102 includes component features, e.g., electron features, for each of the plurality of components and pair features for each of a plurality of pairs of the plurality of components.

As a particular example, for each electron in the chemical system, the electron features can include distance-based features that are based on the relative positions, e.g., the three-dimensional relative positions of the electron and each nucleus of the chemical system. In particular, for a given electron and given nucleus, the electron features can include a difference vector that measures the difference in positions of the given electron and the given nucleus within the chemical system, i.e., a distance vector that is equal to $r_i$-$R_I$, where $r_i$ is the vector representing the position of the i-th electron within the chemical system and $R_I$ is the vector representing the position of the I-th nucleus within the chemical system. Optionally, the electron features can also include the absolute distance between the given electron and the given nucleus, i.e., the norm of the distance vector, in addition to the distance vector.

Further optionally, for each electron in the chemical system, the electron features can also include a feature identifying the spin of the electron, i.e., that identifies whether the electron is a spin-up electron or a spin-down electron.

As another particular example, for each pair of electrons in the chemical system, the pair features can include distance-based features that are based on the relative positions of the electrons in the pair within the chemical system. In particular, the pair features can include a difference vector that measures the difference in positions of the electrons in the pair within the chemical system, i.e., a distance vector that is equal to $r_i$-$r_j$, where $r_i$ is the vector representing the position of the first electron i in the pair within the chemical system and $r_j$ is the vector representing the position of the second electron j in the pair within the chemical system. Optionally, the pair features can also include the absolute distance between the two electrons in the pair, i.e., the norm of the distance vector, in addition to the distance vector.

As the distance between two electrons or an electron and a nucleus is a non-smooth function at zero, the neural network 110 is capable of expressing the non-smooth behavior of the wavefunction when two particles coincide—the wavefunction cusps. Accurately modeling these cusps is important for correctly estimating the energy and other properties of the chemical system. Thus, including the distance vectors and, optionally, the absolute distances as input can assist the neural network 110 in accurately estimating the output property or properties of the chemical system, although the wavefunction can still be approximated without these. Moreover, including the absolute distances between particles directly as input removes the need to include a separate Jastrow factor (representing electron-electron correlations) after a determinant.

Further optionally, for each pair of electrons in the chemical system, the pair features can also include a feature identifying the spin of each of the electrons in the pair, i.e., that identifies whether each electron in the pair is a spin-up electron or a spin-down electron.

As described above, the antisymmetric neural network 110 maps the input data 102 to a predicted value 112 of one or more properties of the system.

The antisymmetric neural network 110 has a plurality of intermediate layers and generates the predicted value 112 from the output of the last intermediate layer in the neural network 110. The intermediate layers are referred to as "intermediate" because the output generated by the intermediate layers, i.e., i.e., the output of the last intermediate layer in the neural network 110, are intermediate features that are used to generate the predicted value 112, i.e., rather than directly being the predicted value 112 that is the output of the neural network 110.

In order to ensure that the outputs of the neural network 110 are antisymmetric, each of the intermediate layers is configured to generate a respective layer output for the intermediate layer from a respective layer input to the intermediate layer by applying a respective permutation-equivariant function to the respective layer input to the intermediate layer.

A permutation-equivariant function, in this context, means that if two layer input features corresponding to different electrons with the same spin are permuted then the corresponding different layer output electron features are permuted in the same way. In other words, if the input streams for two spin up electrons are swapped, the output streams for the two spin up electrons will also be swapped, i.e., relative to the output streams that would be generated had the input streams not been swapped. Similarly, if the input streams for two spin down electrons are swapped, the output streams for the two spin down electrons will also be swapped. Mathematically speaking, the function is equivariant with respect to a subgroup of the group of all electron permutations, i.e., the subgroup is the set of all permutations where the spins of the electrons being permuted are the same.

Once the last intermediate layer has generated the layer output, the neural network 110 generates, from the layer output of the last intermediate layer, a respective input for each of a plurality of determinants, i.e., to each of a plurality of functions that each compute determinants of a different matrix, determines a respective output of each determinant from the respective input for the determinant, and determines the predicted value from the respective outputs of each of the determinants.

Because each intermediate layer that is used to generate the input to the determinant function is permutation-equivariant and because the output of the neural depends on determinants computed from the outputs of these permutation-equivariant functions, the output of the neural network 110, i.e., the predicted value 112, is antisymmetric with respect to the exchange of features of any two components of the input system.

The architecture of the neural network 110 and generating an output from features of a chemical system are described in more detail below with reference to FIGS. 2 and 3.

Figure 2:
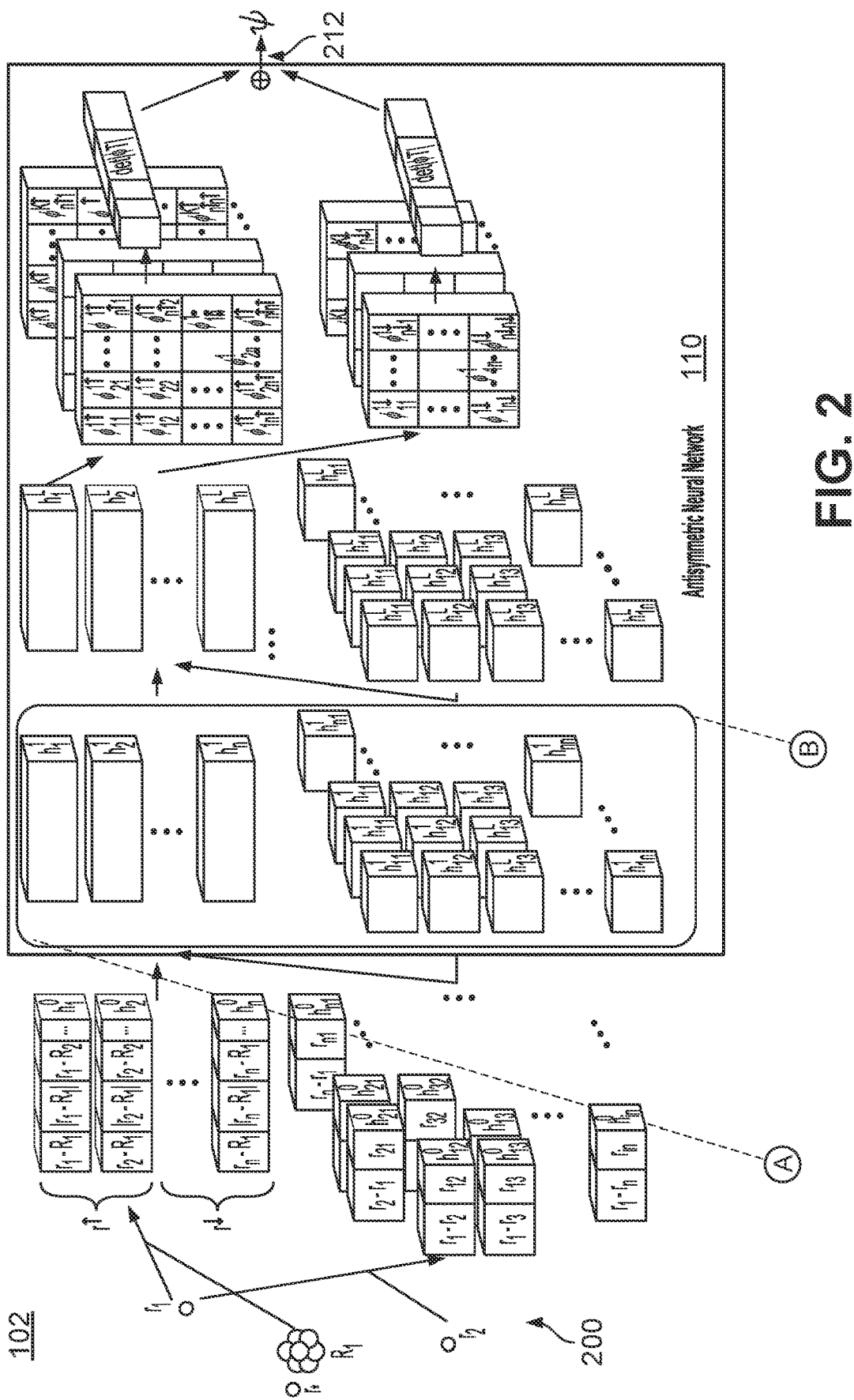
FIG. 2 shows an example architecture of the antisymmetric neural network.
Figure 2:
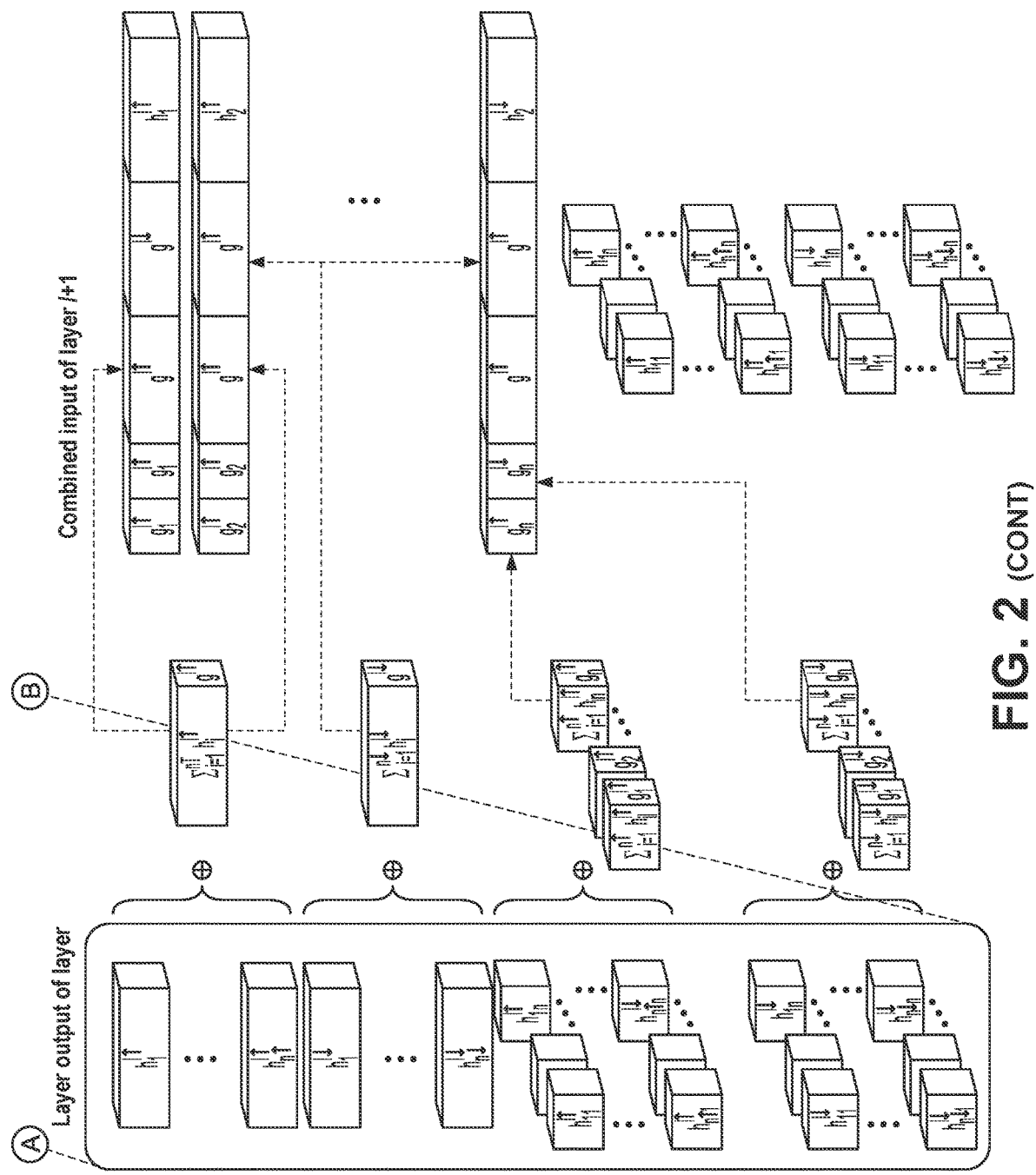

FIG. 2 shows an example architecture of the antisymmetric neural network 110.

In particular, in the example of FIG. 2, input data 102 is generated for a chemical system 200 and the neural network 110 processes the input data 102 to generate a predicted value 212 of the wavefunction of the chemical system 200.

While three electrons $r_1$, $r_2$, and $r_i$ and a single nucleus $R_I$ are shown in FIG. 2 for ease of illustration, it will be understood that the chemical system 200 can have more electrons, more nuclei, or both than what is shown in the Figure.

The input data 102 includes electron features for each of the n electrons in the chemical system 200 and pair features for each pair of (distinct) electrons in the chemical system 200.

In FIG. 2, the electron features in the input data 102 for the i-th electron are denoted as $h_i^0$ while the pair features for a pair of electrons i and j are denoted as $h_{ij}^0$.

Generally, the n electrons are divided into n↑ spin up electrons and n↓ spin down electrons. The spin up electrons are ordered from 1 to n↑ and the spin down electrons are ordered from 1 to n↓ before the input data 102 is processed by the neural network 110.

As described above, the electron features for a given electron r include, for each nucleus R in the chemical system, a distance vector and an absolute distance. The pair features for any given pair of electrons also include a distance vector and an absolute distance.

As shown in FIG. 2, the neural network 110 processes the input data 102 using L intermediate layers 210.

Each of the L intermediate layers receives a layer input and generates a layer output.

For each of the first L−1 intermediate layers, the layer output of the layer is used to generate the layer input to the next layer.

For the last intermediate layer, i.e., intermediate layer L, the layer output of the intermediate layer is used to generate an input to a plurality of determinant functions, as will be described in more detail below.

Generally, for each layer l of the intermediate layers, the respective layer input for the intermediate layer includes a separate input stream $h_i^{l-1}$ for each of the electrons and a separate input stream $h_{ij}^{l-1}$ for each of the pairs of electrons.

Similarly, for each layer l of the intermediate layers, the layer output includes a separate output stream $h_i^l$ for each of the electrons and a separate output stream $h_{ij}^l$ for each of the pairs of electrons.

For the first intermediate layer of the L intermediate layers, i.e., intermediate layer 1, the input stream for each of the electrons is the electron features $h_i^0$ for the electron and the input stream for each of the pairs of electrons is the pair features $h_{ij}^0$ for the pair of electrons.

For each intermediate layer of the L intermediate layer after the first intermediate layer 1, the input stream for each of the electrons is the output stream for the electron generated by the preceding intermediate layer and the input stream for each of the pairs of electrons is the output stream for the pair generated by the preceding intermediate layer.

Each of the intermediate layers is configured to operate on each input stream with a corresponding stream sub-layer, i.e., a sub-layer that is configured to generate the output stream for the corresponding electron or pair of electrons from the input stream for the corresponding electron or pair of electrons.

As will be evident from the description below, because of the use of input streams and corresponding stream sub-layers, each intermediate layer applies a permutation-equi-variant function to the respective layer input for the intermediate layer. In other words, if the order of the input streams were modified, each intermediate layer would still return the same layer output because of the use of the sub-layers.

The operations that occur within a given intermediate layer are shown in FIG. 2 and described below with reference to the operations performed by an intermediate layer l+1. However, more generally, these operations are performed by each intermediate layer (except, in some implementations, for the last intermediate layer as described below).

Within the intermediate layer l+1, each sub-layer that corresponds to one of the electrons (i.e., instead of to one of the pairs of electrons) is configured to receive the input stream for the corresponding electron from the respective layer input, generate a combined input for the corresponding electron from the input streams in the respective layer input, and to generate the output stream for the corresponding electron from the input stream for the electron and the combined input for the electron.

Generally, the sub-layer generates a concatenated input $f_i^l$ for the corresponding electron by concatenating the input stream for the corresponding electron and the combined input for the corresponding electron and then processes the concatenated input to generate a concatenated output stream for the corresponding electron.

In particular, the sub-layer processes the concatenated input by applying a linear transformation to the concatenated input, e.g., by multiplying the concatenated input by a weight matrix for the sub-layer and then optionally adding a learned bias or by performing a convolution between a weight kernel for the sub-layer and the concatenated input, to generate a transformed stream. The sub-layer can then apply a non-linear activation function, e.g., the tanh or rectified linear unit function, to the transformed stream to generate the concatenated output stream (a tanh non-linearity is smooth which can help numerical stability).

In some implementations, the concatenated output stream is the output stream $h_i^{l+1}$ for the corresponding electron.

In some other implementations, however, at least some of the intermediate layers generate an output stream for a given electron that includes the concatenated output stream and a residual output stream generated by the stream sub-layer for the corresponding electron in a preceding intermediate layer, i.e., the output stream $h_i^l$ from the preceding intermediate layer (or, for the first intermediate layer, the electron features for the electron). For example, the output stream for the given electron can be a concatenation, sum, or average of the concatenated output stream and the residual output stream.

As shown in FIG. 2, to generate the combined input for a given electron from the layer output of layer l, the sub-layer corresponding to the electron computes, for each possible electron spin, a respective average of the input streams corresponding to electrons that have the electron spin. In other words, the sub-layer computes (i) the average $g^{l\uparrow}$ of the input streams $h_i^{l\uparrow}$ corresponding to spin up electrons and (ii) the average $g^{l\downarrow}$ of the input streams $h_i^{l\downarrow}$ corresponding to spin down electrons.

The sub-layer then includes the averages in the combined input.

Optionally, the sub-layer can also, for each of the possible electron spins, compute a respective average of the input streams corresponding to pairs of electrons that include both the corresponding electron and an electron that has the possible electron spin. In other words, the sub-layer computes (i) the average $g_i^{l\uparrow}$ of the input streams $h_{ij}^{l\uparrow}$ corresponding to pairs of electrons that include the corresponding electron and a spin up electron and (ii) the average $g_i^{l\downarrow}$ of the input streams $h_{ij}^{l\downarrow}$ corresponding to pairs of electrons that include the corresponding electron and a spin down electron.

The sub-layer then includes the averages in the combined input.

For example, the combined input can be a concatenation of the computed averages, e.g., the averages $g^{l\uparrow}$, $g^{l\downarrow}$, $g_i^{l\uparrow}$, and $g_i^{l\downarrow}$.

Unlike for the individual electrons, for each pair of electrons, the particular stream sub-layer corresponding to the pairs is configured to receive the input stream for the corresponding pair from the respective layer input for the intermediate layer and process the input stream to generate an initial output stream, i.e., without generating a combined or concatenated input.

In some implementations, the initial output stream is the output stream for the corresponding pair.

In some other implementations, for at least one of the intermediate layers, the output stream for a given pair includes the initial output stream for the pair and a residual output stream generated by the stream sub-layer for the given pair in a preceding intermediate layer. For example, the output stream for the given pair can be a concatenation, sum, or average of the concatenated output stream and the residual output stream.

Thus, information from both the other one-electron streams and the pair streams are fed into the one-electron streams. However, to reduce the computational overhead of the neural network 110, no information is transferred between pair streams. These can then be implemented as multilayer perceptrons running in parallel. Because of the architecture of the neural network 110, the neural network 110 can still generate accurate predicted values even with this reduction in computational overhead.

As described above, the neural network 110 uses the layer output of the last intermediate layer L to generate the predicted value that is the output of the neural network 110.

In particular, the neural network 110 generates, from the layer output of the last intermediate layer, a respective input for each of a plurality of determinants and determines a respective output of each determinant from the respective input for the determinant.

Generally, the input to each determinant is a square matrix of values, and the output of the determinant is the determinant of the square matrix. Because, as will be seen from the description below, the input to each determinant is a different matrix, each determinant will generally output a different scalar determinant value.

More specifically, and as shown in FIG. 2, the plurality of determinants include multiple pairs of determinants, with each pair of determinants including one determinant that operates on a matrix generated from output streams for spin up electrons and another determinant that operates on a matrix generated from output streams for spin down electrons. In particular, in the example of FIG. 2 one determinant in each pair operates on a n↑ by n↑ matrix while the other determinant operates on a n↓×n↓ matrix. Each matrix may be antisymmetric in the sense that exchanging the electron features of any two electrons in the input data exchanges two rows or two columns of the matrix.

To generate the input matrix to a given determinant, the neural network 110 applies a final spin-dependent linear transformation to the layer output of the last intermediate layer (and, more specifically, to the output streams for the electrons in the layer output of the last intermediate layer) to generate a final transformed output and then generate the input for the given determinant, i.e., the input matrix for the determinant, based on applying each of a plurality of exponentially-decaying envelopes to some or all of the final transformed output. Applying the exponentially-decaying envelopes enforces the boundary condition that the wavefunction ($\psi$) goes to zero far away from the nuclei.

The linear transformation is referred to as a spin-dependent transformation because, within each pair of determinants, a different transformation is applied to electrons that are spin up than electrons that are spin down to generate the inputs to the determinants in the pair.

In other words, for the k-th pair of determinants, to generate the element ij in the input matrices to the determinants in the pair, the system generates the element ij in the final transformed output for the element ij as follows:

$$t_{ij}^{k\alpha} = w_i^{k\alpha} \cdot h_j^{L\alpha} + g_i^{k\alpha},$$

where $\alpha$ denotes spin up or spin down, $w_i^{k\alpha}$ and $g_i^{k\alpha}$ are weights and biases of the final linear transformation for the k-th pair of determinants (and, because of the dependency on $\alpha$, are different depending on whether the linear transformation is for the spin up matrix or the spin down matrix), and $h_j^{L\alpha}$ is the output stream for the j-th spin up or spin down electron.

The system then applies to $t_{ij}^{k\alpha}$ a weighted sum of exponentially-decaying envelopes to generate the element ij in the input matrix as follows:

$$\phi_{ij}^{k\alpha} = t_{ij}^{k\alpha} \Sigma_m \pi_{im}^{k\alpha} \exp(-|\Sigma_{im}^{k\alpha}(r_j^\alpha - R_m)|),$$

where the sum is over the radii in the chemical system, and $\pi_{im}^{k\alpha}$ and $\Sigma_{im}^{k\alpha}$ are learned parameters that control the anisotropic decay to zero far from each nucleus.

The neural network 110 then determines the predicted value from the respective outputs of each of the determinants. For example, the neural network 110 can determine the predicted value as a weighed sum of the products of, for each pair of determinants, the determinant outputs of the determinants in the pair.

As can be seen from the description above, in some implementations, only the output streams corresponding to the electrons, and not the pairs of electrons, in the layer output of layer L are used to compute the predicted value. Accordingly, in these implementations, the last intermediate layer L may not include sub-layers corresponding to the pairs of electrons (and only include sub-layers corresponding to the individual electrons in the chemical system) and therefore may generate a layer output that includes only output streams for individual electrons and not for any pairs of electrons.

In some cases, the determinants can be computed in the log domain, and the output of the neural network can therefore be the log of the absolute value of the wavefunction and the sign of the wavefunction. This can help to improve numerical stability. In this case, when the system is trained (see later) the energy is computed in the log domain, i.e., as a function of log $\psi$.

Figure 3:
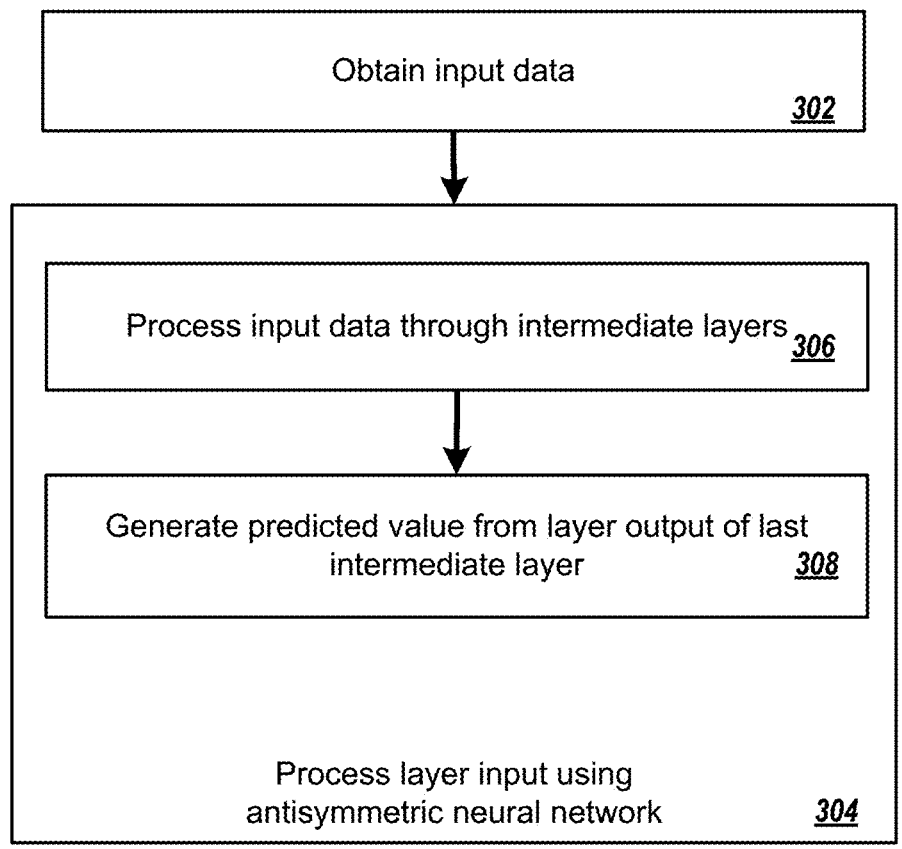
FIG. 3 is a flow diagram of an example process for generating an output for a network input.

FIG. 3 is a flow diagram of an example process 300 for generating a predicted value. For convenience, the process 300 will be described as being performed by a system of one or more computers located in one or more locations. For example, a neural network system, e.g., the neural network system 100 of FIG. 1, appropriately programmed, can perform the process 300.

The system obtains input data characterizing a chemical system with a plurality of electrons (step 302). The input data includes electron features for each of the plurality of electrons and pair features for each of a plurality of pairs of the plurality of electrons. For examples the input data can include pair features for each possible pair of electrons or of a subset of the possible pairs of electrons that can be generated by selecting from the plurality of electrons in the chemical system.

The system processes the input data using an antisymmetric neural network to generate a predicted value for a property of the system (step 304).

More specifically, the antisymmetric neural network is configured to process the input data through a plurality of intermediate layers to generate a layer output for the last intermediate layer (step 306) and then generate the predicted value of the property from the layer output of the last intermediate layer (step 308).

The system can train the antisymmetric neural network to generate accurate predicted values of the property of the subject system on training data to minimize an objective function using an appropriate gradient-descent based training technique. The objective function can be any appropriate objective function for the particular task that the neural network is being trained to perform and generally measures errors between predicted values generated by the neural network for training input data and a known or target value for the property for the system characterized by the training input data.

As a particular example, when the property is a wavefunction of a chemical system, the objective function can be a loss function that measures the energy expectation value of the wavefunction Ansantz, i.e., the system can train the neural network to generate predicted wavefunction values that minimize the energy expectation value of the wavefunction Ansantz.

Where determinants are computed in the log domain a gradient of the objective function (energy), L, with respect to parameters $\theta$ of the antisymmetric neural network can be determined as $$\nabla_\theta L = (E_L - E_{p(X)}[E_L]) \nabla_\theta \log|\psi|$$

where X the set of 3D coordinates for all the electrons, $p(X) \propto \psi_\theta^2(X)$, and $E_L$ evaluated for $\psi(X)$ can be determined as $$E_L(X) = -\frac{1}{2} \sum_i \left[ \frac{\partial^2 \log|\psi|}{\partial r_i^2} + \left(\frac{\partial \log|\psi|}{\partial r_i}\right)^2 \right] + V(X)$$

where V(X) is the potential energy of state X and index i runs over each of the three dimensions for each electron of X.

As one example of a gradient-based technique that can be used to train a neural network optimize such an objective, the system can train the neural network using a version of Kronecker Factorised Approximate Curvature (KFAC), which is an approximation to a natural gradient descent technique appropriate for training neural networks.

Merely by way of illustration, in some implementations the number of intermediate layers may be small e.g., less than 10 or less than 5. The width of the set of streams for the electrons may be less than 100 hidden units, though this may depend on the number of electrons and in general using more hidden units may increase the accuracy.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method comprising:
   obtaining input data characterizing a chemical system having a plurality of nuclei and a plurality of electrons, the input data comprising electron features for each of the plurality of electrons and pair features for each of a plurality of pairs of the plurality of electrons; and
   processing the input data using an antisymmetric neural network having a plurality of intermediate layers, wherein:
   the antisymmetric neural network is configured to process the input data to generate as output a predicted value of one or more properties of the chemical system, the one or more properties comprising one or more of a wavefunction of the chemical system or a ground state energy of the chemical system,
   each of the plurality of intermediate layers of the antisymmetric neural network is configured to generate a respective layer output for the intermediate layer from a respective layer input to the intermediate layer by applying a respective permutation-equivariant function to the respective layer input,
   the antisymmetric neural network is configured to generate the predicted value from the respective layer output of the last intermediate layer of the plurality of intermediate layers,
   a respective layer output of a last intermediate layer of the plurality of layers comprises a respective output stream for each of the plurality of electrons,
   generating the predicted value comprises:
      generating, from the respective layer output of the last intermediate layer, a respective input for each of a plurality of pairs of determinants, each pair of determinants including (i) one determinant that operates on a respective spin up matrix that is generated from respective output streams for spin up electrons and has a respective row and a respective column for each of the spin up electrons and (ii) another determinant that operates on a respective spin down matrix generated from respective output streams for spin down electrons and has a respective row and a respective column for each of the spin down electrons, and wherein each pair of determinants of the plurality of determinants has respective spin down and spin up matrices that are different from each other pair of determinants of the plurality of determinants;
      determining a respective output of each determinant in the plurality of pairs of determinants from the respective input for the determinant; and determining the predicted value from the respective outputs of each of the determinants in the plurality of pairs of determinants, and the antisymmetric neural network has been trained on training data to optimize at least a variational energy objective.

2. The method of claim 1, wherein, for an intermediate layer:

the respective layer input comprises a separate input stream for each of the electrons and for each of the pairs of electrons, the layer output comprises a separate output stream for each of the electrons and for each of the pairs of electrons, and the intermediate layer is configured to operate on each input stream with a corresponding stream sub-layer.

3. The method of claim 2, wherein, for a first intermediate layer of the plurality of intermediate layers, the input stream for each of the electrons is the electron features for the electron and the input stream for each of the pairs of electrons is the pair features for the pair of electrons.

4. The method of claim 2, wherein, for each of the plurality of intermediate layers, the particular stream sub-layer corresponding to each of the electrons is configured to:

receive the input stream for the corresponding electron from the respective layer input;

generate a combined input for the corresponding electron from the input streams from the respective layer input;

concatenate the input stream generated by the particular stream sub-layer with the combined input to generate a concatenated input stream for the corresponding electron; and process the concatenated input stream to generate a concatenated output stream for the corresponding electron.

5. The method of claim 4, wherein the concatenated output stream is the output stream for the corresponding electron.

6. The method of claim 4, wherein, for at least one of the intermediate layers, the output stream for the corresponding electron includes the concatenated output stream and a residual output stream generated by the stream sub-layer for the corresponding electron in a preceding intermediate layer.

7. The method of claim 4, wherein processing the concatenated input stream to generate a concatenated output stream comprises:

applying a linear transformation to the concatenated input stream to generate a transformed stream; and applying a non-linear activation function to the transformed stream to generate the concatenated output stream.

8. The method of claim 4, wherein generating a combined input for the corresponding electron comprises:

for each of a plurality of electron spins, computing an average of the input streams corresponding to electrons that have the electron spin; and including the averages in the combined input.

9. The method of claim 8, wherein generating a combined input for the corresponding electron comprises:

for each of the plurality of electron spins, computing an average of the input streams corresponding to pairs of electrons that include the corresponding electron and an electron that has the electron spin; and including the averages in the combined input.

10. The method of claim 2, wherein for each of the plurality of intermediate layers, the particular stream sub-layer corresponding to each of the pairs is configured to:

receive the input stream for the corresponding pair from the respective layer input for the intermediate layer; and process the input stream to generate an initial output stream.

11. The method of claim 10, wherein the initial output stream is the output stream for the corresponding pair.

12. The method of claim 10, wherein, for at least one of the intermediate layers, the output stream for the corresponding pair includes the initial output stream and a residual output stream generated by the stream sub-layer for the corresponding pair in a preceding intermediate layer.

13. The method of claim 1, wherein the electron features include a difference vector that measures a difference in positions of the electron and a nucleus within the system.

14. The method of claim 13, wherein the electron features include a norm of the difference vector.

15. The method of claim 1, wherein the electron features include a feature identifying a spin of the electron.

16. The method of claim 1, wherein the pair features include a difference vector that measures a difference in positions between the electrons in the pair within the system.

17. The method of claim 16, wherein the pair features include a norm of the difference vector.

18. The method of claim 1, wherein the pair features include a feature identifying spins of the electron in the pair.

19. The method of claim 1, wherein generating, from the layer output of the last intermediate layer, a respective input for each of a plurality of pairs of determinants comprises, for each pair of determinants:

applying a first final spin-dependent linear transformation to the respective output streams for the spin up electrons to generate a final transformed output for the spin up electrons;

generating the respective spin-up matrix for the determinant in the pair that operates on the spin up electrons based on applying a plurality of exponentially-decaying envelopes to some or all of the final transformed output for the spin up electrons, wherein applying the exponentially-decaying envelopes enforces a boundary condition that the wavefunction of the chemical system goes to zero away from the nuclei of the chemical system;

applying a second final spin-dependent linear transformation to the respective output streams for the spin down electrons to generate a final transformed output for the spin down electrons; and generating the respective spin-down matrix for the other determinant in the pair that operates on the spin down electrons based on applying the plurality of exponentially-decaying envelopes to some or all of the final transformed output for the spin down electrons.

20. A system comprising one or more computers and one or more non-transitory storage devices storing instructions that when executed by the one or more computers cause the one or more computers to perform operations comprising:

obtaining input data characterizing a chemical system having a plurality of nuclei and a plurality of electrons, the input data comprising electron features for each of the plurality of electrons and pair features for each of a plurality of pairs of the plurality of electrons; and processing the input data using an antisymmetric neural network having a plurality of intermediate layers, wherein:

the antisymmetric neural network is configured to process the input data to generate as output a predicted value of one or more properties of the chemical system, the one or more properties comprising one or more of a wavefunction of the chemical system or a ground state energy of the chemical system, each of the plurality of intermediate layers of the antisymmetric neural network is configured to generate a respective layer output for the intermediate layer from a respective layer input to the intermediate layer by applying a respective permutation-equivariant function to the respective layer input, the antisymmetric neural network is configured to generate the predicted value from the respective layer output of the last intermediate layer of the plurality of intermediate layers, a respective layer output of a last intermediate layer of the plurality of layers comprises a respective output stream for each of the plurality of electrons, generating the predicted value comprises:
  generating, from the respective layer output of the last intermediate layer, a respective input for each of a plurality of pairs of determinants, each pair of determinants including (i) one determinant that operates on a respective spin up matrix that is generated from respective output streams for spin up electrons and has a respective row and a respective column for each of the spin up electrons and (ii) another determinant that operates on a respective spin down matrix generated from respective output streams for spin down electrons and has a respective row and a respective column for each of the spin down electrons, and wherein each pair of determinants of the plurality of determinants has respective spin down and spin up matrices that are different from each other pair of determinants of the plurality of determinants;
  determining a respective output of each determinant in the plurality of pairs of determinants from the respective input for the determinant; and
  determining the predicted value from the respective outputs of each of the determinants in the plurality of pairs of determinants, and the antisymmetric neural network has been trained on training data to optimize at least a variational energy objective.

21. One or more non-transitory computer-readable storage media storing instructions that when executed by one or more computers cause the one or more computers to perform operations comprising:
  obtaining input data characterizing a chemical system having a plurality of nuclei and a plurality of electrons, the input data comprising electron features for each of the plurality of electrons and pair features for each of a plurality of pairs of the plurality of electrons; and
  processing the input data using an antisymmetric neural network having a plurality of intermediate layers, wherein:
    the antisymmetric neural network is configured to process the input data to generate as output a predicted value of one or more properties of the chemical system, the one or more properties comprising one or more of a wavefunction of the chemical system or a ground state energy of the chemical system, each of the plurality of intermediate layers of the antisymmetric neural network is configured to generate a respective layer output for the intermediate layer from a respective layer input to the intermediate layer by applying a respective permutation-equivariant function to the respective layer input, the antisymmetric neural network is configured to generate the predicted value from the respective layer output of the last intermediate layer of the plurality of intermediate layers, a respective layer output of a last intermediate layer of the plurality of layers comprises a respective output stream for each of the plurality of electrons, generating the predicted value comprises:
      generating, from the respective layer output of the last intermediate layer, a respective input for each of a plurality of pairs of determinants, each pair of determinants including (i) one determinant that operates on a respective spin up matrix that is generated from respective output streams for spin up electrons and has a respective row and a respective column for each of the spin up electrons and (ii) another determinant that operates on a respective spin down matrix generated from respective output streams for spin down electrons and has a respective row and a respective column for each of the spin down electrons, and wherein each pair of determinants of the plurality of determinants has respective spin down and spin up matrices that are different from each other pair of determinants of the plurality of determinants;
      determining a respective output of each determinant in the plurality of pairs of determinants from the respective input for the determinant; and
      determining the predicted value from the respective outputs of each of the determinants in the plurality of pairs of determinants, and the antisymmetric neural network has been trained on training data to optimize at least a variational energy objective.

22. The system of claim 20, wherein, for an intermediate layer:
  the respective layer input comprises a separate input stream for each of the electrons and for each of the pairs of electrons,
  the layer output comprises a separate output stream for each of the electrons and for each of the pairs of electrons, and
  the intermediate layer is configured to operate on each input stream with a corresponding stream sub-layer.

23. The system of claim 22, wherein, for a first intermediate layer of the plurality of intermediate layers, the input stream for each of the electrons is the electron features for the electron and the input stream for each of the pairs of electrons is the pair features for the pair of electrons.

* * * * *